United States Patent [19]

Kurono et al.

[11] Patent Number: 4,528,184
[45] Date of Patent: Jul. 9, 1985

[54] POLYMER-METAL COMPLEXES CONTAINING QUATERNARY NITROGEN ATOMS USED IN THE TREATMENT OF HYPERCHOLESTEREMIA

[75] Inventors: Masayasu Kurono; Osamu Nakagawa, both of Nagoya; Takafumi Iida, Kasugai; Yoshiro Ishiwata, Nagoya; Tomio Ogasawara, Nagoya; Meiji Kuwayama, Nagoya, all of Japan

[73] Assignee: Kabushiki Kaisha Vitamin Kenkyuso, Kasugai, Japan

[21] Appl. No.: 438,487

[22] Filed: Nov. 2, 1982

[30] Foreign Application Priority Data

Nov. 4, 1981 [JP] Japan .................................. 56-175741

[51] Int. Cl.³ ............................................. A61K 31/74
[52] U.S. Cl. ........................................ 424/79; 424/78; 525/47; 525/389; 525/540
[58] Field of Search .................. 424/78, 79; 525/47, 525/389, 540

[56] References Cited

U.S. PATENT DOCUMENTS 3,692,895 9/1972 Nelson et al. ........................ 424/78

FOREIGN PATENT DOCUMENTS 2036048 6/1980 United Kingdom .

Primary Examiner—Leonard Schenkman
Assistant Examiner—Joseph A. Lipovsky
Attorney, Agent, or Firm—Charles A. Muserlian

[57] ABSTRACT

A novel polymer-metal complex containing quaternary nitrogen atoms, which is obtained by subjecting polyethylenepolyamine or polyethyleneimine to a reaction with a bifunctional compound represented by the formula $$Y-A-Z$$

wherein Y and Z are same or different and are $-CH_2X$, $-CH(OH)CH_2X$ or

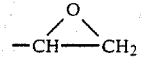

group, respectively, A is a single bond, $-(CH_2)_m-$, $-CH_2-O-CH_2-$ or $-CH_2-O-(CH_2)_k-O-CH_2-$ group, X is chlorine, bromine or iodine atom, m is an integral of 1 to 3, and k is an integral of 1 to 4, and then subjecting the resulting cross-linked polymer to a coordination of a polyvalent metal ion, a salt thereof, a process for the preparation thereof and a pharmaceutical agent comprising the same.

22 Claims, No Drawings

POLYMER-METAL COMPLEXES CONTAINING QUATERNARY NITROGEN ATOMS USED IN THE TREATMENT OF HYPERCHOLESTEREMIA

This invention relates to a novel polymer-metal complex containing quaternary nitrogen atoms, salt thereof, process for preparation thereof, and use of same as the effective component for hypercholesterolemia treating agents.

A group of substances which lower the levels of cholesterol in the serum and liver by disturbing the adsorption of bile acids, i.e. metabolites of cholesterol in digestive tracts, has theretofore been considered as a kind of arteriosclerosis treating agents. As such substances, the cross-linked polymers formed by introducing quaternary nitrogen atoms into a cross-linked polymer of styrene and divinyl benzene, and those of tetraethylenepentamine and epichlorohydrin were found to be useful (U.S. Pat. Nos. 2,272,489 and 3,692,895). Besides, a polymer containing ammonium salts made up of lower alkyl groups and 20% or more nitrogens of a cross-linked polymer consisting of polyethylenepolyamine and epichlorohydrin has been disclosed in Jap. Unexamined Pat. Appln. Official Gazette No. 66,513/1980.

Although these compounds were recognized as hypercholesterolemia treating agents, their side effects such as constipation still remain as problems to be solved.

Therefore, the fundamental purpose of the present invention is to provide polymers and pharmaceutically acceptable salts thereof which lower serum cholesterol levels without issuance of any substantial side effect. According to the present invention, this purpose can be attained by synthesizing a novel polymer-metal complex and pharmaceutically acceptable salt thereof. The polymer-metal complex having quaternary nitrogen atoms (20 to 80% of all nitrogen atoms), are produced by the coordination of polyvalent metal ions to a cross-linked polymer to be obtained by subjecting polyethylenepolyamine or polyethyleneimine to the reaction with a bifunctional compound represented by the general formula;

$$Y-A-Z$$

wherein Y and Z are same or different and are —CH$_2$X, —CH(OH)CH$_2$X or

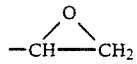

group, respectively, A is a single bond, —(CH$_2$)$_m$—, —CH$_2$—O—CH$_2$— or —CH$_2$—O—(CH$_2$)$_k$—O—CH$_2$— group, X is chlorine, bromine or iodine, m is an integral of 1 to 3, and k is an integral of 1 to 4.

The incidental object of this invention is to provide a process for the preparation of such polymer-metal complex and pharmaceutically acceptable salt thereof.

According to the invention, this object is accomplished by the following processes: polyethylenepolyamine or polyethyleneimine is reacted with the bifunctional compound to form a cross-linked polymer which is further treated with polyvalent metal ions to form a metal cross-linked polymer, the metal cross-linked polymer is treated with an N-tertiarizing agent and then with an N-quaternarizing agent to provide finally a polymer-metal complex containing quaternary nitrogen atoms (20 to 80% of the total nitrogen). If necessary, the polymer-metal complex is made into the pharmaceutically acceptable corresponding salt.

As the polyethylenepolyamines, straight chain compounds such as ethylenediamine, diethylenetriamine, triethylenetetramine and tetraethylenepentamine can be used, and especially tetraethylenepentamine is recommended. It is preferable for polyethylenepolyamine to have the degree of the repeating unit range of 2–10 and the average molecular weight range of 103–477.

As the polyethyleneimines, compounds having straight or branched chains can be used. They have the degree of the repeating unit range of 930–1163, preferably 1000. It is preferred to have the average molecular weight range of 40000–50000.

As the bifunctional compounds, epichlorohydrin, 1,3-dichloro-2-hydroxypropane, 1,2:3,4-diepoxybutane, bisepoxypropylether etc. can be used, and especially epichlorohydrin is preferred. As to the ratio of polyethylenepolyamine or polyethyleneimine to bifunctional compound, the number of the molecule of given bifunctional compound should be more than $$\left( \frac{1}{10} + \frac{1}{n+1} \right)$$

and less than (n+2) to the number of the molecule of polyethylenepolyamine or polyethyleneimine, wherein n represents the degree of repeating unit of polyethylenepolyamine or polyethyleneimine.

As the coordinating polyvalent metal ions, ferric ion or aluminium ion is preferred, because it is essential for these metal ions to be able to make a stable coordinate bond with an unshared electron pair of the nitrogen atoms in the cross-linked polymer.

As a substituent providing the tertiary or quaternary nitrogen atom, methyl, ethyl, propyl, isopropyl, butyl, allyl, 2-butenyl, isobutenyl, benzyl, p-methylbenzyl, p-chlorobenzyl, p-hydroxybenzyl, 4-hydroxy-3-methoxy cinnamyl, or a similar group can be used. Quarternary nitrogen atoms may have single or mixed substituents of the above groups. Although the nitrogen atoms of the cross-linked polymer are quaternarized by 20–80%, it is recommended that the nitrogen atoms are quaternarized by 40–70% in order to maintain good physical properties and to provide high ability to adsorb cholic acid. The residual nitrogen atoms may exist in primary, secondary and tertiary forms, but the tertiary form is preferred.

The pharmaceutically acceptable corresponding salts mean those of an inorganic acid such as hydrocholic acid, phosphoric acid, carbonic acid, etc., those of an organic acid such as acetic acid, lactic acid, tertaric acid, citric acid, etc., those of an amino acid such as glycine, alanine, etc. or those of an aminosulfonic acid such as taurine, homotaurine, etc.

It is well-known that a cross-linked polymer can be obtained by subjecting a nitrogen containing compound consisting of ethylenediamine or polyethylenepolyamine having the degree of repeating unit range of 2–1500 to the reaction with a bifunctional compound such as epichlorohydrin (U.S. Pat. Nos. 2,272,489, 3,692,895, and Canadian Pat. No. 687,254). Since these well-known cross-linked polymers are chelate compounds, it is disadvantageous that the polymers frequently adsorb microelements which are essential for human bodies, when orally administered.

According to the present invention, such shortage of these well-known polymers is completely conquered by introducing the concept of metal coordination.

In order to obtain the cross-linked polymer, the nitrogen containing compound of polyethylenepolyamine or polyethyleneimine is cross-linked with a certain bifunctional compound in a conventional organic solvent or water.

In order to obtain the metal cross-linked polymer, the cross-linked polymer is treated, in general, with an aqueous metal salt such as metal chloride. In the case of coordinating ferric ion, it is preferable to use polybasic-carbonic acid such as citric acid, because of the special ability, due to polybasic acid, to maintain the suitable condition for stable metal coordinate bond formation.

Among the various methods for quaternarizing 20–80% of the nitrogen atoms in the metal cross-linked polymer, the most popular one is to treat with alkylating agent, e.g., methyl iodide and methyl chloride. Repeating this alkylation, the proportion of the quaternary nitrogen atoms increases gradually. In the case of N-quaternarization with methyl group, it is more preferable that the metal cross-linked polymer is initially tertiarized as much as possible and then quaternarized with methyl iodide or methyl chloride.

The amount of quaternary nitrogen atom can be controlled by changing the ratio of an alkylating agent to the metal cross-linked polymer. The other type of polymer-metal complexes carrying two or more substituents on quarternary nitrogen atom are easily obtained by using additional benzylhalide and/or allylhalide as other kinds of alkylating agent.

The polymer-metal complexes obtained by the above-mentioned method have more stable structure due to the metal chelate bond formation than the corresponding usual non-metal chelate polymer. This fact is also supported by the evidence that this cross-linked polymer can be converted to a polymer-metal complex quantitatively by quaternarization. This is the reason why the polymer-metal complexes do not adsorb essential metal ions, when administered orally. As shown in Example 7 (in vitro test), the polymer-metal complexes do not adsorb vitamins and essential amino acids. Moreover, they don't cause constipation, probably because of their hydrophilic nature. These properties led us to use the polymer-metal complex as a hypercholesterolemia treating agent safely, since these agents are often used for a long time continuously.

As shown in Example 6, the polymer-metal complexes have strong affinity to cholic acid due to their large amount of quaternary nitrogen atoms. Moreover, as shown in Example 8 (in vivo test using hypercholesterolemic rats), the administration of polymer-metal complexes greatly improved the levels of low-density lipoprotein cholesterol (LDL-cholesterol), high-density lipoprotein cholesterol (HDL-cholesterol) and atherogenic index.

As acute toxicity test, the polymer-metal complexes were administered to rats orally at the rate of 20 g/kg of body weight (wet volume; 142 ml/kg of body weight). The volume was maximum one which can be introduced into the stomach of rat. None of the rats died and autopsy revealed no signs in toxication. Accordingly, the actual $LD_{50}$ could not be determined (see Example 9).

When these polymer-metal complexes are administered to rats at the dosage of 10 g/kg of body weight/day with daily diet for 14 days continuously, no signs in toxication was found by autopsy (see Example 9).

In the case of affected man, the total daily dosage of the polymer-metal complex or pharmaceutically acceptable salt thereof ranges from about 1 g to about 50 g, preferably from about 1 g to about 20 g. The preferred regimen of the oral administration is three to four times daily.

The polymer-metal complexes or their pharmaceutically acceptable corresponding salts of the present invention may be used in any form combined with any carrier which can be administered orally. Examples of such carrier are solid or liquid medical base materials as well as beverage and food. Representative examples of the solid medical base materials are lactose, sugar, dextrin, glucose, mannitol, etc. Examples of the oral dosage forms are powders, granules, capsules, pills, and coated and uncoated tablets.

The following Examples illustrate the present invention.

EXAMPLE 1

Step 1-a

Cross-linking polymerization of polyethyleneimine and epichlorohydrin

To dispersion of 7.00 kg of 30% polyethyleneimine-water solution having 1000 average degree of repeating unit in 15.0 kg of chlorobenzene, 0.757 kg of epichlorohydrin was added dropwise at 20°–30° C. The reaction mixture was stirred at 50° C. for 4 h and refluxed for 5 h. After the reaction, the resulting product was separated from the chlorobenzene solution and washed with 2N-NaOH solution followed by deionized water to give the cross-linked polymer (Sample 1-a). Physical properties of the Sample 1-a are shown below.

Water content: 70.00%
Weak base exchange capacity: 9.62 mEq/g

Step 1-b

Adsorption of Fe (III) ion with Sample 1-a

Suspension of 4844 g of Sample 1-a (1453 g, as dried weight) in 48.5 L of deionized water containing 655 g of $FeCl_3.6H_2O$ (2.423 mol) and 1425 g of $Na_3C_6H_5O_7.2H_2O$ (4.845 mol) was stirred at 21°–25° C. for 21 h. The reaction product was filtered and washed with deionized water to give 4700 g (1897 g as dried weight) of the metal coordinated polymer (Sample 1-b) in 130.6 weight percent yield. The concentration of ferric ion was measured before and after the reaction, and then the amount of ferric ion which was adsorbed to the Sample 1-b was determined to be 1037 mmol. Physical properties of the Sample 1-b are shown below.

Water content: 59.64%
Iron content: 0.547 mmol/g
Strong base exchange capacity: 0.84 mEq/g
Weak base exchange capacity: 8.96 mEq/g

Step-1-c

Tertiarization of Sample 1-b with formic acid-formaldehyde

A mixture of 2300 g of Sample 1-b (928 g as dried weight) with 7360 mL of ethanol, 2245 g of formic acid and 1840 g of 36% formaldehyde in water, was heated under stirring at 85° to 90° C. for 22 h. The reaction mixture was cooled, filtered and then washed with deionized water. The residue was treated with 55 L of 1N-NaOH solution and then washed with deionized water to give 2340 g (725.5 g as dried weight) of the metal coordinated polymer (Sample 1-c), of which the amino group was tertiarized completely (with 78.1 weight percent yield). Measurement of the concentration of ferric ion in the filtrate shown 103.8 mmol of ferric ion were losed from the polymer during the reaction. Physical properties of the metal coordinated polymer (Sample 1-c) are shown below.
Water content: 69.01%
Iron content: 0.557 mmol/g
Strong base exchange capacity: 0.64 mEq/g
Weak base exchange capacity: 7.92 mEq/g
Consumption of the reagent;
Formic acid: 13.51 mol
Formaldehyde: 8.48 mol Step 1-d Quaternarization of Sample 1-c with allyl bromide A mixture of 550 g of Sample 1-c (170.4 g as dried weight) with 2200 mL of ethanol and 206.2 g of allyl-bromide was stirred at 50° C. for 14 h. After being filtered and washed with 100 mL of methanol (4 times) followed by 70 mL of water (3 times), the product was treated with steam, and then washed with 17 L of deionized water and 5 L of 5% NaCl solution and again 5 L of deionized water to give 920 g (215 g as dried weight) of the polymer-metal complex (Sample 1-d) having chloride anion as a counter anion of the resin polymer. Physical properties of the obtained polymer-metal complex (Sample 1-d) are shown below.
Water content: 76.63%
Iron content: 0.448 mmol/g
Strong base exchange capacity: 3.63 mEq/g
Weak base exchange capacity: 3.31 mEq/g

EXAMPLE 2

Quaternarization of Sample 1-c with methyl iodide

A mixture of 548.6 g of Sample 1-c (170.0 g as dried weight) with 219.5 mL of methanol and 241.3 g of methyl iodide was stirred at 50° C. for 17 h. The resulting product was filtered and washed with 100 mL of methanol (4 times) followed by 70 mL of deionized water (3 times). The product was treated with steam for 5 h and then washed with 14 L of 2N—NaOH solution followed by 17 L of deionized water. The product was further treated successively with 5 L of 5% NaCl solution and washed with 5 L of deionized water to give 1449 g of the polymer-metal complex (Sample 2) having a chloride anion as a counter anion of the resin polymer (203.5 g as dried weight, with 119.8 weight percent yield). Physical properties of the polymer (Sample 2) are shown below.
Water content: 85.96%
Iron content: 0.460 mmol/g
Strong base exchange capacity: 4.37 mEq/g
Weak base exchange capacity: 2.78 mEq/g

EXAMPLE 3

Quaternarization of Sample 1-c with benzyl bromide

A mixture of 15.0 g of Sample 1-c (4.45 g as dried weight) with 60.0 mL of methanol and 7.62 g of benzyl bromide is stirred at 50° C. for 5 h. The reaction mixture is filtered and washed with 10 mL of methanol (4 times) and 10 ml of deionized water (3 times). After treatment with steam, the product is washed with 2 L of 2N—NaOH solution and treated with 1 L of deionized water, and then treated with 1 L of 4% NaCl solution and finally washed with 1 L of deionized water. The invented polymer-metal complex, 17.6 g (Sample 3), having a chloride ion as a counter anion of the polymer is obtained (6.33 g as dried weight, with 142.2 weight percent yield). Physical properties of the polymer-metal complex (Sample 3) are shown below.
Water content: 64.03%
Iron content: 0.392 mmol/g
Strong base exchange capacity: 3.22 mEq/g
Weak base exchange capacity: 2.64 mEq/g

EXAMPLE 4

Step 4-a

Adsorption of Al (III) ion with Sample 1-a

Suspension of 25.0 g of Sample 1-a (8.28 g as dried weight) in 100 mL of deionized water containing 2.27 g of $AlCl_3.6H_2O$ (9.40 mmol) was stirred at 15°–20° C. for 16 h. The reaction product was filtered and washed with deionized water and then with 250 mL of 2N-NaOH solution and with deionized water to give 22.0 g (7.94 g as dried weight) of the metal coordinated polymer (Sample 4-a) with 95.9 weight percent yield. Physical properties of the Sample 4-a are shown below.
Water content: 63.91%
Adsorption of Al (III) ion: 0.360 mmol/g
Strong base exchange capacity: 0.85 mEq/g
Weak base exchange capacity: 9.00 mEq/g Step 4-b Quaternarization of Sample 4-a with methyl iodide A mixture of 10.0 g of Sample 4-a (3.36 g as dried weight) with 60.0 mL of methanol and 5.80 g of methyl iodide was stirred at 50° C. for 6 h. The reaction mixture was filtered and washed with 10 mL of methanol (4 times), 10 mL of deionized water (3 times), 800 mL of 1N-NaOH solution and then 500 mL of deionized water. A mixture of the resulting product with 60 mL of methanol and 5.80 g of methyl iodide was stirred at 50° C. for 6 h. The reaction mixture was filtered and washed with 10 mL of methanol (4 times), 10 mL of deionized water (3 times), 800 mL of 1N-NaOH solution, 500 mL of deionized water, 800 mL of 4% NaCl solution and then 500 mL of deionized water. The intended polymer-metal complex, 26.7 g (4.00 g as dried weight) having a chloride as a counter anion of the polymer, was obtained (Sample 4-b) with 119.0 weight percent yield. Physical properties of the polymer-metal complex (Sample 4-b) are shown below.
Water content: 85.02%
Aluminium content: 0.339 mmol/g
Strong base exchange capacity: 4.38 mEq/g
Weak base exchange capacity: 2.80 mEq/g

EXAMPLE 5

Step 5-a

Cross-linking polymerization of tetramethylenepentamine and epichlorohydrin

A mixture of 756 g of tetraethylenepentamine, 9 L of deionized water and 463 g of epichlorohydrin was stirred at 25° C. for 1 h. The reaction mixture was cooled to 30° C. and 300 mL of 50% NaOH solution and 463 g of epichlorohydrin were added thereto and then the mixture was stirred at 25° C. for 1 h and at 90° C. for 5 h. The reaction mixture was acidified to be pH 6 and treated with ethanol. The resulting product was washed with ethanol, dried, powdered with mill and swelled with deionized water to give the cross-linked polymer (Sample 5-a). Physical properties of the Sample 5-a are shown below.

Water content: 84.69%
Weak base exchange capacity: 8.50 mEq/g

Step 5-b

Adsorption of Fe (III) ion with Sample 5-a

A suspension of 26.0 g of Sample 5-a (6.27 g as dried weight) in 130 mL deionized water containing 1.743 g of $FeCl_3.6H_2O$ (6.448 mmol) and 3.823 g of $Na_3C_6H_5O_7.2H_2O$ (13.0 mmol) was stirred at 20°–30° C. for 14 h. The reaction mixture was filtered and washed with deionized water, and then treated with 11.42 g of $Na_3C_6H_5O_7.2H_2O$ in 125 mL of deionized water solution. The resulting mixture was filtered and washed with deionized water to give 24.1 g (7.77 g as dried weight) the metal coordinated polymer (Sample 5-b) with 123.9 weight percent yield. Physical properties of the Sample 5-b are shown below.

Water content: 67.76%
Iron content: 0.770 mmol/g
Strong base exchange capacity: 0.26 mEq/g
Weak base exchange capacity: 8.30 mEq/g Step 5-c Tertiarization of Sample 5-b with formic acid-formaldehyde A mixture of 6.15 g of Sample 5-b (1.98 g as dried weight) with 5.06 mL of isopropanol, 4.50 g of formic acid and 3.25 g of 36% formaldehyde in water, was stirred at 85° to 90° C. for 22 h. The reaction mixture was cooled, filtered and then washed with deionized water. The product was treated with 500 mL of 1N-NaOH solution and then washed with deionized water to give 7.102 g (1.761 g as dried weight) of the metal-coordinated polymer (Sample 5-c), of which the amino groups were tertiarized (with 88.9 weight percent yield). Measurement of the concentration of ferric ion of the filtrate showed 0.450 mmol losed from polymer during the reaction. Physical properties of the metal coordinated polymer (Sample 5-a) are shown below.

Water content: 75.20%
Iron content: 0.610 mmol/g
Strong base exchange capacity: 0.67 mEq/g
Weak base exchange capacity: 7.66 mEq/g
Consumption of the reagent;
Formic acid: 36.4 mmol
Formaldehyde: 11.1 mmol Step 5-d Quaternarization of Sample 5-c with methyl iodide A mixture of 4.782 g of Sample 5-c (1.186 g as dried weight) with 19.0 mL of methanol and 1.680 g of methyl iodide was stirred at 50° C. for 18 h. After being filtered and washed with 12 mL of methanol (4 times) followed by 10 mL of deionized water (3 times), the product was treated with steam, and then washed with 500 mL of 1N-NaOH solution and 2.5 L of deionized water and 1 L of 4%-NaCl solution and again 1.3 L of deionized water to give 31.48 g (1.278 g as dried weight) of the polymer-metal complex (Sample 5-d) having chloride ion as a counter anion of the resin polymer with 107.8 weight percent yield. Physical properties of the polymer-metal complex (Sample 5-d) are shown below.

Water content: 95.94%
Iron content: 0.567 mmol/g
Strong base exchange capacity: 3.568 mEq/g
Weak base exchange capacity: 2.053 mEq/g

EXAMPLE 6

The adsorbing ability of the invented polymers toward cholic acid

The adsorbing ability of Sample 1-a, 1-d, 2, 3, 4-b, 5-a and 5-d toward cholic acid is measured as follows. Each sample was ground in a mortar and an aliquot of a specified amount was taken. The aliquot was buffered with 20 mL of phosphate buffer (pH 7.50; so called artificial intestinal juice) to give each sample suspension. 20 mL of phosphate-buffered sodium cholate solution (1.000 mmol/20.0 mL) was added to each sample suspension. After the mixture was stirred at 35° C. for 1 h, each sample solution was subjected to a centrifugal separation and then an amount of cholic acid remaining therein was measured to determine the amount of cholic acid adsorbed by the sample. The results are summarized in Table 1.

TABLE 1

| | Capacity for Adsorption of Sodium Cholate | |
|---|---|---|
| Samples | Dry weight* (mg) | Total exchange capacity (mEq) |
| 1-a | 260 | 2.50 |
| 1-d | 190 | 1.32 |
| 2 | 145 | 1.04 |
| 3 | 225 | 1.32 |
| 4-b | 142 | 1.02 |
| 5-d | 189 | 1.06 |

*Minimum weight for 50% adsorption of sodium cholate (1.0 mmol) at pH 7.5.

EXAMPLE 7

Adsorption of vitamins and essential amino acids by the invented polymer

The adsorption of Sample 2 toward vitamins and essential amino acids was measured as follows. One hundred milligrams of Sample 2 was added to 20 ml of the solution of vitamin $B_1$, vitamin $B_2$, lysine or tryptophan buffered with 20 mL of phosphate buffer. Each mixed solution was stirred at 37° C. After 1 h, the suspension was separated into supernatant liquid and resin residue by filtration. The vitamins and amino acids were analyzed quantitatively by routine methods. The results are summarized in Table 2. Vitamin $B_1$, vitamin $B_2$, lysine and tryptophan, respectively, were quantitatively recovered.

TABLE 2

| | Recovery of Vitamins and Essential Amino Acids | | | |
|---|---|---|---|---|
| | Vitamin $B_1$[a] | Vitamin $B_2$[b] | Tryptophan[c] | Lysine[d] |
| Blank | 100.0 | 100.0 | 100.0 | 100.0 |
| Test solution | 100.0 | 99.7 | 96.6 | 99.9 |

[a] 20 μg/20 ml as thiamin hydrochloride.
[b] 50 μg/20 ml
[c] 4 mg/20 ml
[d] 4 mg/20 ml
After stirring with 100 mg of the invented polymer-metal complex at 37° C. for 1 h, the each sample was analyzed quantitatively.

EXAMPLE 8

Test for the effects of lowering the levels of serum lipids of rats

Sample 1-d and 2 in Example 1-d and 2 were tested on their effects of lowering the levels of serum lipids.

Five-weeks old male Wister rats, weighing between 120 and 140 g, were divided into groups of 10 rats each. Two groups were served as control groups, the other groups are served as test groups and the other two groups are served as normal groups. The normal groups were fed with a commercially available diet (CA-1 diet manufactured by Nippon CLEA Co.). The control groups and the test groups were fed with a cholesterol-rich diet for two weeks to appear rats suffering from hyperchlesterolemia. The rats with hypercholesterolemia were divided into the control and test groups. The rats of control group were fed with the cholesterol-rich diet and each test group was fed with the cholesterol-rich diet containing 1% of each sample, for two weeks. The diet was given at 10 g/100 g of body weight/day ad libitum. The body weight, serum total cholesterol, serum LDL-cholesterol and serum HDL-cholesterol were measured, before and after feeding, on each of normal group, control group and test group, and then atherogenic index (LDL-cholesterol/HDL-cholesterol) was calculated from values on LDL-cholesterol and HDL-cholesterol. The results are summarized in Tables 3 and 4.

From the results of the test, it can be seen as shown in Tables 3 and 4 that Sample 1-d and 2, as compared with control group, remarkedly exhibit the effect to prevent experimental hypercholesterolemia in rats induced by a cholesterol-rich diet. The oral administration of these invented compounds at the rate of 1000 mg/kg of body weight/day for two weeks shows remarkable lowering of serum total cholesterol levels and LDL-cholesterol levels as well as remarkable increase of HDL-cholesterol levels. In addition, these two samples remarkably exhibit the effect to improve atherogenic index.

TABLE 3

Effects of Sample 2 and 1-d on the Body Weight and the Levels of Serum Cholesterol of Rats fed with a Cholesterol-Rich Diet for 14 Days

| | Regimen | No. of rats | Body weight (g) Before (on 2 wks.) | Body weight (g) After (on 4 wks.) | Body weight (g) Gain (g/14 days) | Serum total cholesterol (mg/dl) Before | Serum total cholesterol (mg/dl) After |
|---|---|---|---|---|---|---|---|
| Normal group | Normal diet (10 g/100 g b.w.) | 10 | 187.7[1] ± 2.1 | 283.7 ± 4.4 | 96.0 ± 3.3 | 80.1*[2] ± 3.4 | 91.9* ±3.9 |
| Control group | Cholesterol rich diet (10 g/100 g b.w.) | 10 | 179.6 ± 1.0 | 281.6 ± 4.6 | 102.1 ± 4.5 | 650.7 ± 33.5 | 437.0 ± 20.0 |
| Test group with Sample 2 | Cholesterol rich diet + Sample 2 (1 g/kg/day) | 10 | 185.9 ± 2.7 | 292.8 ± 7.5 | 106.9 ± 5.3 | 650.7 ± 33.5 | 143.3* ± 3.9 |
| Test group with Sample 1-d | Cholesterol rich diet + Sample 1-d (1 g/kg/day) | 10 | 183.0 ± 2.0 | 283.2 ± 5.3 | 100.2 ± 4.1 | 650.7 ± 33.5 | 141.9* ± 9.0 |

[1]Mean S.E. is given.
[2]Significant difference from the control group by Student's t-test (*$p < 0.001$).

TABLE 4

Effects of Sample 2 and 1-d on the Levels of Serum LDL-Cholesterol and HDL-Cholesterol and Atherogenic Indexes of Rats fed with a Cholesterol Rich Diet for 14 Days

| | No. of rats | Serum LDL[1]-cholesterol (mg/dl) Before | Serum LDL[1]-cholesterol (mg/dl) After | Serum HDL[2]-cholesterol (mg/dl) Before | Serum HDL[2]-cholesterol (mg/dl) After | [3]Atherogenic index Before | [3]Atherogenic index After |
|---|---|---|---|---|---|---|---|
| Normal group | 10 | 21.3* ± 2.3 | 12.9*[4] ± 1.4 | 47.5*[5] ± 2.6 | 62.4* ± 2.3 | 0.46* ± 0.06 | 0.21* ± 0.02 |
| Control group | 10 | 553.4 ± 26.2 | 414.6 ± 24.0 | 20.2 ± 1.8 | 20.8 ± 3.0 | 29.33 ± 2.72 | 23.89 ± 3.86 |
| Test group with Sample 2 | 10 | 553.4 ± 26.2 | 37.8* ± 2.5 | 20.2 ± 1.8 | 94.1* ± 3.7 | 29.33 ± 2.72 | 0.41* ± 0.03 |
| Test group with Sample 1-d | 10 | 553.4 ± 26.2 | 55.9* ± 9.6 | 20.2 ± 1.8 | 72.2* ± 5.4 | 29.33 ± 2.72 | 0.88* ± 0.23 |

[1]LDL: low-density lipoproteins.
[2]HDL: high-density lipoproteins.
[3]Atherogenic index = serum LDL-cholesterol/serum HDL-cholesterol.
[4]Means ± S.E. is given.
[5]Significant difference from the control group by Student's t-test (*$p < 0.001$).

EXAMPLE 9

Toxicity test of the invented polymer-metal complex (a) Acute toxicity test

Five-weeks old male Wister rats, weighing 130 to 140 g, were divided into two groups. A group is served as a control group and the other group as test group. Rats of the test group were orally administered with the invented polymer-metal complex at the rate of 20 g/kg of body weight (wet volume: 142 ml/kg of body weight) after fasted overnight. Rats of the two groups were fed with a commercially available CA-1 diet ad libitum for a week. None of the rats died and autopsy revealed no sign of toxicity. More than 20 g (as dried weight) of the polymer-metal complexes could not be administered, because of the limiting of the stomach of usual rat. So the LD$_{50}$ of the invented polymer-metal complex could not be determined.

(b) Short-term high-dose test

Five-weeks old male Wistar rats, weighing 130–140 g, were divided into two groups. A group is served as test group and the other as control group. The rats of control group were fed with CA-1 diet and test group fed with the diet containing 10% of the invented polymer-metal complex (equivalent to 10 g/kg of body weight/day), for two weeks. The diet was given at 10 g/100 g of body weight/day.

None of the rats died and autopsy revealed no sign of toxicity. Moreover, no side effect such as constipation was observed.

We claim:

1. A hypercholesteremia treating composition comprising an hypercholesterolemically effective amount of a polymer-metal complex in which the polymer component is a cross-linked polymer of a polyethylenepolyamine or polyethyleneimine and a bifunctional compound represented by the formula

Y—A—Z where Y and Z are individually selected from the group consisting of —CH$_2$X, —CH(OH)CH$_2$X and

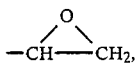

A is selected from the group consisting of a single bond, —(CH$_2$)m—, —CH$_2$—O—CH$_2$— and —CH$_2$O—(CH$_2$)$_k$—O—CH$_2$—, X is a chlorine, bromine or iodine atom, m is an integer of 1 to 3, and K is an integer of 1 to 4, and the metal component is a polyvalent metal ion coordinated in said cross-linked polymer, said complex having 20 to 80% of the total nitrogen atoms quaternized, or a non-toxic, pharmaceutically acceptable acid addition salt thereof, said composition being in the form of an orally administerable dosage of a powder, granule, capsule or tablet.

2. The composition as claimed in claim 1, wherein said polyethylenepolyamine is tetraethylenepentamine.

3. The composition as claimed in claim 1, wherein said polyethyleneimine has about 1000 repeating units.

4. The composition as claimed in claim 1, wherein said bifunctional compound is epichlorohydrin.

5. The composition as claimed in claim 1, wherein said polyvalent metal ion is ferric or aluminum ion and the amount of such ion is 0.01 to 1.0 mmol/g of the dried polymer-metal complex.

6. The composition as claimed in claim 1, wherein said quaternary nitrogen atoms have any one or more substituents or methyl, allyl and benzyl groups.

7. The composition as claimed in claim 1, wherein the ratio of polyethylenepolyamine or polyethyleneimine and the bifunctional compound is that the number of molecule of said bifunctional compound is from $$\left( \frac{1}{10} + \frac{1}{n+1} \right)$$

to (n+2) to the number of molecule of polyethylenepolyamine or polyethyleneimine, in which n represents the degree of repeating unit of polyethylenepolyamine or polyethyleneimine.

8. A method of treating hypercholesterolemia in warm-blooded animals comprising administering to warm-blooded animals a hypercholesterolemically effective amount of a complex of claim 1.

9. The method of claim 8 wherein said polyethylenepolyamine is tetraethylenepentamine.

10. The method of claim 8 wherein said polyethyleneimine has about 1000 repeating units.

11. The method of claim 8 wherein said bifunctional compound is epichlorohydrin.

12. The method of claim 8 wherein said polyvalent metal ion is ferric or aluminum ion and the amount of such ion is 0.01 to 1.0 mmol/g of the dried polymer-metal complex.

13. The method of claim 8 wherein said quaternary nitrogen atoms have any one or more substituents of methyl, allyl and benzyl groups.

14. The method of claim 8 wherein the ratio of polyethylenepolyamine or polyethyleneimine and the bifunctional compound is that the number of molecule of said bifunctional compound is from $$\left( \frac{1}{10} + \frac{1}{n+1} \right)$$

to (n+2) to the number of molecule of polyethylenepolyamine or polyethyleneimine, in which n represents the degree of repeating unit of polyethylenepolyamine or polyethyleneimine.

15. A process for the preparation of a polymer-metal complex of claim 1 comprising the steps of reacting a polyethylenepolyamine or polyethyleneimine with a bifunctional compound of the formula

Y—A—Z wherein Y and Z are defined as in claim 1 to obtain a cross-linked polymer, reacting the acid cross-linked polymer with a polyvalent metal ion, reacting the resulting metal coordinated cross-linked polymer with a tertializing agent and then with a quaternarizing agent to form the polymer-metal complex containing quaternary nitrogen atoms in 20 to 80% of the total nitrogen atoms, and optionally converting the complex into its non-toxic, pharmaceutically acceptable acid addition-salt.

16. The process as claimed in claim 15, wherein said polyethylenepolyamine is tetraethylenepentamine.

17. The process as claimed in claim 15, wherein said polyethyleneimine has about 1000 repeating units.

18. The process as claimed in claim 15, wherein said bifunctional compound is epichlorohydrin.

19. The process as claimed in claim 15, wherein said polyvalent metal ion is ferric or aluminum ion and the amount of such ion is 0.01 to 1.0 mmol/g of the dried polymer-metal complex.

20. The process as claimed in claim 15, wherein said coordination of ferric ion is carried out in the presence of a polybasic carboxylic acid.

21. The process as claimed in claim 15, wherein said quaternization of nitrogen atoms is carried out by bonding any one or more substituents of methyl, allyl and benzyl groups.

22. The process as claimed in claim 15, wherein the ratio of polyethylenepolyamine or polyethyleneimine and the bifunctional compound is that the number of molecule of said bifunctional compound is from $$\left(\frac{1}{10} + \frac{1}{n+1}\right)$$

to (n+2) to the number of molecule of polyethylenepolyamine or polyethyleneimine, in which n represents the degree of repeating unit of polyethylenepolyamine or polyethyleneimine.

* * * * *